United States Patent
Jensen et al.

(10) Patent No.: US 6,194,568 B1
(45) Date of Patent: Feb. 27, 2001

(54) PROCESS FOR SYNTHESIZING CARBAPENEM INTERMEDIATES

(75) Inventors: Mark S. Jensen, Holmdel; Yi Xiao, Fanwood; Chunhua Yang, Edison; Kenneth M. Wells, Neshanic Station; Nobuyoshi Yasuda, Mountainside, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/326,762

(22) Filed: Jun. 4, 1999

Related U.S. Application Data

(60) Provisional application No. 60/092,631, filed on Jul. 13, 1998.

(51) Int. Cl.$^7$ .............................. C07D 477/14; C07F 7/18
(52) U.S. Cl. ............................................................ 540/302
(58) Field of Search ........................ 514/210.09; 540/302

(56) References Cited

U.S. PATENT DOCUMENTS

| | | | |
|---|---|---|---|
| 4,350,631 | * | 9/1982 | Christensen et al. ................. 546/272 |
| 4,994,568 | * | 2/1991 | Christensen ........................... 540/302 |
| 5,756,725 | * | 5/1998 | Wilkening et al. ................... 540/302 |

FOREIGN PATENT DOCUMENTS

| | | |
|---|---|---|
| 0 102 239 | 3/1984 | (EP) . |
| 0 212 404 A1 | 3/1987 | (EP) . |
| 0 330 108 | 8/1989 | (EP) . |
| 0 476 649 A1 | 3/1992 | (EP) . |
| 0 695 753 A1 | 8/1994 | (EP) . |

OTHER PUBLICATIONS

Funk, J. Organic Chemistry 51, 3247, 1986.*
Yasuda et al., Tetrhedron Letters 34: 3211–3214 (1993).

* cited by examiner

*Primary Examiner*—Mark L. Berch
(74) *Attorney, Agent, or Firm*—Sylvia A. Ayler; Mark R. Daniel

(57) ABSTRACT

The invention describes an improved process for synthesizing 1-β-methyl-2-hydroxymethyl substituted carbapenems as key intermediates for the synthesis of anti-MRSA carbapenem antibiotics. The synthesis eliminates the use of $BU_3SnCH_2OH$ and HMPA, which are toxic substances and not amenable to industrial scale production. The novel intermediates are also within the scope of this invention.

The invention relates to the synthesis of a compound of formula 3:

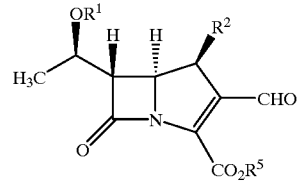

wherein $R^1$ represents H or a suitable protecting group for an alcohol; $R^2$ represents H or methyl; and $R^5$ represents a carboxy protecting group as well as the compounds made therein.

32 Claims, No Drawings

PROCESS FOR SYNTHESIZING CARBAPENEM INTERMEDIATES

This application claims the benefit of U.S. Privisional Application Ser. No. 60/092613, filed Jul. 13, 1998.

BACKGROUND OF THE INVENTION

The invention described herein relates to a process for synthesizing 1β-methyl-2-hydroxymethyl carbapenem intermediate compounds that are useful in the synthesis of carbapenems. Generally the carbapenems are substituted at the 2-position. The intermediate compounds are included as well.

European applications 0330108, 0102239, 0212404, 0695753 and 0476649 disclose methods for synthesizing various antibiotic derivatives. Likewise, U.S. Pat. No. 4,350,631 issued to Christensen, et al. on Sep. 21, 1982 and in U.S. Pat. No. 4,994,568 issued to Christensen on Feb. 19, 1991 also discloses various antibiotic derivatives and methods of making.

Many of the carbapenems are useful against gram positive microorganisms, especially methicillin resistant Staphylococcus aureus (MRSA), methicillin resistant Staphylococcus epidermidis (MRSE), and methicillin resistant coagulase negative Staphylococci (MRCNS). These antibacterials thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

The invention describes an improved process for synthesizing 1β-methyl-2-hydroxymethyl substituted carbapenems as key intermediates for the synthesis of anti-MRSA carbapenem antibiotics. Previously, intermediates of 1p-methyl-2-hydroxymethyl substituted carbapenems were prepared by a Stille-type cross-coupling reaction using BuSnCH$_2$OH and HMPA (see U.S. Ser. No. 60/056967, filed Aug. 26, 1997, Merck case number 19988PV). This new synthesis eliminates the use of Bu$_3$SnCH$_2$OH and HMPA. The novel intermediates are also within the scope of this invention.

DETAILED DESCRIPTION OF THE INVENTION

The present invention relates to a process for making 1β-methyl-2-hydroxymethyl substituted carbapenems which are key intermediates in the synthesis of anti-MRSA carbapenem antibiotics (such as those disclosed in U.S. Pat. No. 5,756,725, issued May 26, 1998, the teachings of which are hereby incorporated by reference). The intermediates can be readily coupled to a wide range of functional groups (see U.S. Pat. No. 5,756,725).

In one aspect of the invention, a process of synthesizing a compound of formula 3:

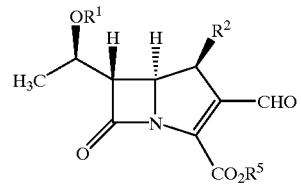

3 is disclosed wherein
$R^1$ represents H or a suitable protecting group for an alcohol; $R^2$ represents H or methyl; and $R^5$ represents a carboxy protecting group
comprising adding a compound of formula 2:

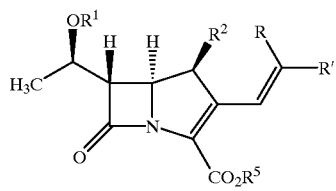

2 wherein
$R^1$, $R^2$ and $R^5$ are described above and R and R' independently represent H, alkyl, O-alkyl, S-alkyl, N-alkyl, O-aryl, S-aryl, N-aryl, or aryl; said alkyl or aryl optionally substituted with 1–3 groups of N, S, O, and halo;
to a solvent in the presence of a catalyst to produce a compound 3.

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "O-alkyl" refers to an oxygen atom attached to an alkyl such as an alkoxy.

The term "N-alkyl" refers to a nitrogen atom attached to an alkyl.

The term "S-alkyl" refers to an sulfur atom attached to an alkyl.

Aryl refers to aromatic rings e.g., phenyl, substituted phenyl and the like as well as rings which are fused, e.g., naphthyl, phenanthrenyl and the like. An aryl group thus contains at least one ring having at least 5 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

Aryl also refer to heteroaryl, which is a monocyclic aromatic hydrocarbon group having 5 or 6 ring atoms, or a polycyclic aromatic group having 8 to 16 atoms, containing at least one heteroatom, O, S, S(O), $SO_2$ or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole and the like.

The term "S-aryl" refers to an sulfur atom attached to an aryl.

The term "N-aryl" refers to an nitrogen atom attached to an aryl.

The term "Oaryl" refers to an oxygen atom attached to an aryl.

Examples of polycyclic heteroaromatics include benzopyrans, benzofurans, benzopyrroles, benzimidazoles, benzothiazoles, quinolines, purines, isoquinolines, benzopyrimidines, dibenzofurans, dibenzothiophenes, 1,8-naphthosultams, The term "heterocycle" (heterocyclyl) refers to a 5–16 membered cycloalkyl group (nonaromatic) with 1–4 rings, in which one of the carbon atoms in the ring is replaced by a heteroatom selected from O, S or N, and in which up to three additional carbon atoms may be replaced by heteroatoms.

The term "heteroatom" means O, S, S(O), $S(O)_2$ or N, selected on an independent basis.

Halogen and "halo" refer to bromine, chlorine, fluorine and iodine.

When a group is termed "protected", such as $R^1$, $R^5$ and the like, this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, N.Y. (1991). Examples of suitable protecting groups are contained throughout the specification.

In some of the compounds of the present invention, $R^1$ and $R^5$ represent alcohol and carboxyl protecting groups, respectively. These groups are generally removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups $R^5$ include allyl, benzhydryl, 2-naphthylmethyl, benzyl, silyl groups such as t-butyldimethylsilyl (TBDMS), trimethylsilyl, (TMS), triethylsilyl (TES), phenacyl, p-methoxybenzyl, o-nitrobenzyl, p-methoxyphenyl, p-nitrobenzyl (pNB), 4-pyridylmethyl and t-butyl, preferably pNB.

Examples of suitable alcohol protecting groups $R^1$ include trialkylsilyl, diarylalkylsilyl, aryldialkylsilyl or trityl such as TMS, TES, TBDMS, carbonates and alkyl carbonates such as benzyl carbonate, benzyl ether, diarylalkylsilyl, aryldialkylsilyl and the like. Preferred $R^1$ groups are TMS, TES, TBDMS.

In still another aspect of the process the synthesis of a compound of formula 4:

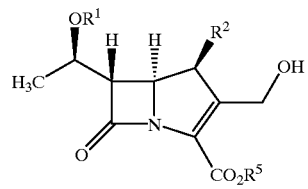

is disclosed wherein
$R^1$ represents H or a suitable protecting group for an alcohol; $R^2$ represents H or methyl; and $R^5$ represents a carboxy protecting group
comprising adding a compound of formula 2:

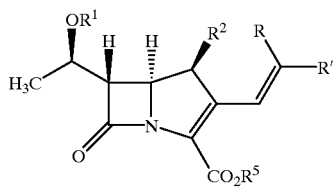

wherein
$R^1$, $R^2$ and $R^5$ are described above and R and R' independently represent H, alkyl, O-alkyl, S-alkyl, N-alkyl, O-aryl, S-aryl, N-aryl, or aryl; said alkyl or aryl optionally substituted with 1–3 groups of N, S, O, and halo;
to a solvent in the presence of a catalyst to produce a compound 3:

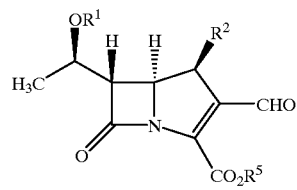

wherein
$R^1$, $R^2$ and $R^5$ are described above;
reducing a compound of formula 3 with a reducing agent to produce a compound of formula 4.

Suitable catalyst include $RuCl_3$, $RuO_2$, $K_2OsO_4 \cdot 2H_2O$, $KMnO_4$, $OsO_4$ and the like or a combination thereof. The catalyst employed is generally from about 0.3 mol % to about 25 mol % of compound 2.

Suitable solvents for the invention disclosed herein include tetrahydrofuran (THF), ethyl acetate (EtOAc), $H_2O$, $C_{1-6}$ alcohol, dichloromethane, acetonitrile, acetone and the like or a combination thereof, preferably THF or THF-$H_2O$.

Suitable reducing agents are $Cp_2TiCl_2/NaBH_4$, $ZnCl_2/NaBH_4$, $BH_3 \cdot SMe_2$, $BH_3 \cdot THF$ and the like.

In another aspect of the invention the process optionally contains from about 0.1 to about 15, preferably about 0.5 to about 6 equivalents, of an oxidizing agent representing $NaIO_4$, $HIO_4$, N-methylmorpholine N-oxide (NMO)-$NaIO_4$, $NaIO_4$-$HIO_4$, and the like, or a combination thereof.

The reaction is conducted at a temperature of about 0° C. to about 80° C., preferably about 15° C. to about 45° C. and most preferably about 20° C. to about 35° C.

In particular, processes of interest are those described above wherein R and R' are hydrogen or R is H and R' is $CH_2OH$.

In the case where $R^1$ is TBS, it is preferable that the catalyst is $OsO_4$, $RuCl_3$ and the like or a combination thereof. When an oxidant is employed it is preferable that it is $NaIO_4$, $HIO_4$ or $NaIO_4$-$HIO_4$. The preferable temperature range is from about 20° C. to about 30° C., most preferably about room temperature.

In the case where $R^1$ is TES, it is preferable that the catalyst is $OsO_4$, or $K_2OsO_4 \cdot 2H_2O$. When an oxidant is employed it is preferable that it is $NaIO_4$, $HIO_4$, NMO-$NaIO_4$. The preferable temperature range is from about 20° C. to about 30° C., most preferably about room temperature. It is further preferred that the pH of the reaction be maintained at about 4 to about 8, more preferably at about 5 to about 7.

In still another aspect of the invention where $R^1$ is TES the process optionally contains a base representing pyridine, triethylamine, triethylamine, trimethylamine, ethyldimethylamine, tri-n-propylamine, 1,8-diazabicyclo[5.4.0]undec-7-ene (DBU), pyridine, imidazole, lutidine, collidine, 4-dimethylaminomethylpyridine, N,N,N',N'-tetramethylethylenediamine (TMEDA), N-methylmorpholine (NMM) and the like.

In yet another aspect of the invention a process for making a compound of formula 3:

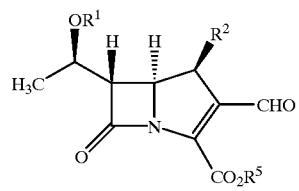

3 is disclosed wherein $R^1$ represents H or a suitable protecting group for an alcohol; $R^2$ represents H or methyl; and $R^5$ represents a carboxy protecting group comprising reacting a compound of formula 2:

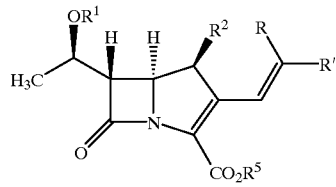

2 wherein $R^1$, $R^2$ and $R^5$ are described above and R and R' independently represent H, alkyl, O-alkyl, S-alkyl, N-alkyl, O-aryl, S-aryl, N-aryl, or aryl; said alkyl or aryl optionally substituted with 1–3 groups of N, S, O, and halo; with a first oxidant in the presence of a catalyst and acid (or buffer to control pH) to yield a compound of formula 5:

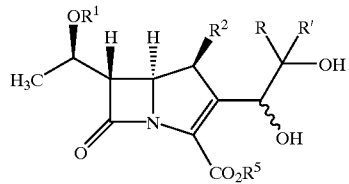

5 wherein

R, R', $R^1$, $R^2$ and $R^5$ are described above; and reacting a compound of formula 5 with a second oxidant to produce the compound of formula 3.

A suitable first oxidant represents a mild oxidant such as N-methylmorpholine N-oxide (NMO), or NMM-$NaIO_4$ (about 1 to about 4 equivalents of the catalyst).

A suitable second oxidant represents a strong oxidant such as $NaIO_4$ or $HIO_4$.

A suitable acid represents acetic acid, 4-morpholinepropanesulfonic acid (MOPS), morpholineethanesulfonic acid (MES) and the like, from about 1 to about 6 equivalents.

In still another aspect of the process the synthesis of a compound of a formula 2:

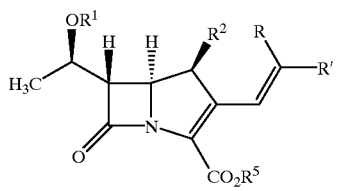

2 is disclosed wherein $R^1$, $R^2$, $R^5$, R and R' are as described above, comprising reacting a compound of formula 1b:

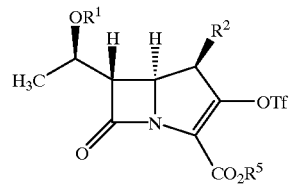

1b with a borate and water mixture wherein the borate is represented by structural formula 1c or 1d:

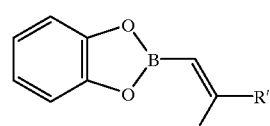

1c

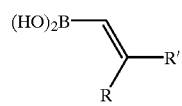

1d wherein R and R' are described above, in the presence of a base and a palladium catalyst to produce a compound of formula 2.

Compound 1b can be made by methods known in the art and exemplified in U.S. Ser. No. 60/056967, filed Aug. 26, 1997, Merck case number 19988PV, herein incorporated by reference.

Suitable bases include $C_{1-6}$ alkylamines such as diisopropyl amine, t-butyl amine, methylamine, hexylamine, ethylamine, triethylamine, diisopropylethylamine, trimethylamine, ethyldimethylamine, tri-n-propylamine and the like, 1,8-diazabicyclo[5.4.0]undec-7-ene (DBU), pyridine, imidazole, lutidine, collidine, 4-dimethylaminomethylpyridine, inorganic carbonates and bicarbonates such as sodium carbonate, sodium bicarbonate, potassium bicarbonate, potassium carbonate, and the like and tartrates such as potassium sodium tartrate, potassium tartrate, potassium bitartrate, sodium tartrate, sodium bitartrate and the like.

Suitable palladium catalyst include $Pd(OAc)_2$, $Pd(PPh_3)_4$ $PdCl_2$, $PdCl_2(PPh_3)_2$, $PdCl_2(CH_3CN)_2$ and $Pd_2dba_3$, and the like, wherein dba is dibenzylideneacetone.

In still another aspect of the invention a compound of formula 3 is disclosed:

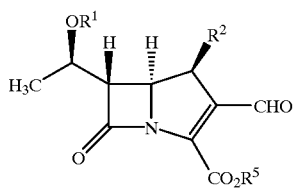

wherein
R$^1$ represents TES, TMS or TBS, R$^2$ represents $C_{1-3}$ alkyl and R$^5$ represents PNB.

The process of the present invention is illustrated by the following generic scheme:

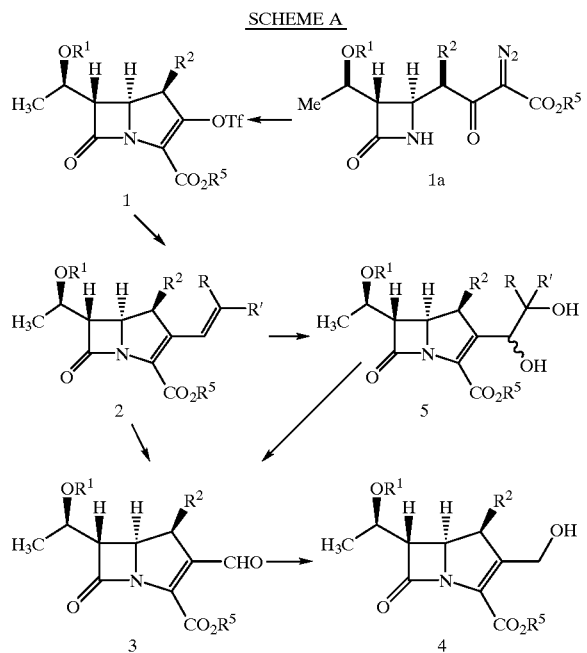

The 2-vinyl compound (compound 2) is synthesized from compound 1, which is readily available by Stille cross-coupling and can be suitably protected by a number of synthetic methods.

Typical conditions for the reaction involve transforming the 2-vinyl compound to its aldehyde (compound 3) using cleavage oxidation catalyzed by about 0.3 mol % to about 25 mol %, preferably about 4.0 mol % to about 12 mol % of a catalyst such as $RuCl_3$, $RuO_2$, $K_2OsO_4.2H_2O$, $KMnO_4$, $OSO_4$ or a combination thereof. About 0.5 to 15.0 equivalents, preferably 2 to 6 equivalents of oxidant is preferably added. The oxidant can be a single entity or a complex such as $NaIO_4$-$HIO_4$, in which case the ratio of $NaIO_4$ and $HIO_4$ ranges from about 5 to 0 to 1 to 1, respectively.

The final product may be characterized structurally by techniques such as NMR, IR, MS, and UV. For ease of handling, the final product, if not crystalline, may be lyophilized from water to afford an amorphous, easily handled solid.

The compounds of the present invention are valuable intermediates for antibacterial agents that are active against various Gram-positive and to a lesser extent Gram-negative bacteria, and accordingly find utility in human and veterinary medicine.

Many of the compounds that can be made in accordance with the present invention are biologically active against MRSA/MRCNS. In vitro antibacterial activity is predictive of in vivo activity when the compounds are administered to a mammal infected with a susceptible bacterial organism.

The invention is further described in connection with the following non-limiting examples.

EXAMPLE 1

Preparation of 2-vinyl carbapenem (2)

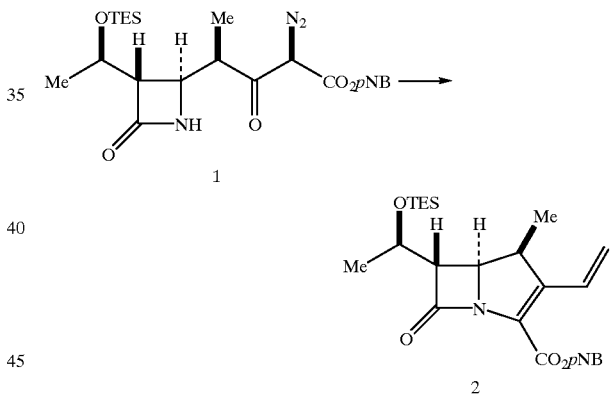

A solution of commercially available diazo compound 1 (1.0 g), zinc chloride (2 mg) and rhodium octanoate (9 mg) in dry dichloromethane (5 mL) was refluxed for 4 h. The solution was cooled to −75° C. and diisopropylamine (0.28 mL) and triethylamine (0.10 mL) were added. After 10 min, trifluoromethanesulfonic anhydride (0.35 mL) was added keeping the internal temperature below −65° C. The reaction mixture was stirred at −75° C. for 2 h. To this solution was added a solution of $Pd_2(dba)_2$ (168 mg) in dry THF (8 mL) at −75° C.

In a separate flask, vinylmagnesium chloride (15 wt % in THF; 4.8 mL) was added to a solution of triisopropylborate (0.92 mL) in dry THF (12 mL) at −5° C. The reaction mixture was aged at −5° C. for 1 h and at 22° C. for 1 h. The mixture was transferred to the above triflate solution. Water (12 mL) was added to the mixture at −40° C. The reaction mixture was aged at 0° C. for 1 h and at 22° C. for 1 h.

The reaction mixture was diluted with t-butyl methyl ether (50 mL). The organic layer was separated, washed with water (3×50 mL) and concentrated in vacuo to obtain a residue, which was chromatographed on silica gel using ethyl acetate and hexanes (1:4 to 1:2) as eluant to give 2-vinyl carbapenem 2 (484 mg) in 50.0% isolated yield as a crystalline solid.

mp: 82.0–83.0° C.

$^1$H NMR (250 MHz, CDCl$_3$): δ8.22 (m, 2H), 7.67 (d, J=8.7 Hz, 2H), 7.37 (dd, J=17.8 and 10.9 Hz, 1H), 5.57 (dd, J=17.8 and 1.0 Hz, 1H), 5.50 (dd, J=11.0 and 1.0 Hz, 1H), 5.46 (d, J=13.9 Hz, 1H), 5.27 (d, J=13.9 Hz, 1H), 4.25 (quint, J=6.2 Hz, 1H), 4.19 (dd, J=9.3 and 2.8 Hz, 1H), 3.40 (dq, J=9.0 and 7.5 Hz, 1H), 3.23 (dd, J=6.1 and 2.7 Hz, 1H), 1.29 (d, J=6.2 Hz, 3H), 1.22 (d, J=7.4 Hz, 3H), 0.94 (t, J=7.9 Hz, 9H), 0.60 (m, 6H)

$^{13}$C NMR (62.9 MHz, CDCl$_3$): δ172.9, 160.8, 149.0, 147.5, 142.9, 128.9, 128.1, 125.7, 123.7, 121.8, 66.0, 65.2, 59.2, 56.3, 39.0, 22.6, 16.7, 6.8, 4.9.

EXAMPLE 2

Preparation of diborate (3)

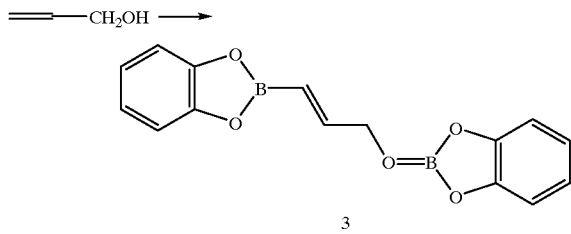

A three-necked-flask equipped with a mechanical stirrer, a 500 mL dropping funnel, a reflux condenser, a thermocouple and a nitrogen inlet was charged with propargyl alcohol (140 mL) and toluene (350 mL). The colorless solution was cooled to 0° C. and catecholborane (300 mL) was added over 45 minutes keeping the internal temperature below 20° C. Caution: vigorous hydrogen evolution! When the hydrogen evolution ceased the cold bath was replaced with a heating mantel and the solution was warmed to 70° C. The remaining catecholborane was added over 1 h and the solution was held at 110° C. for 10 h. The reaction mixture contained a 3.8:1 mixture of 3 and its regioisomer by $^1$H NMR. Toluene (350 mL) was added and the solution was cooled to 5° C. at the rate of −10° C./h. A large crop of colorless crystals developed at about 80° C. The solids were collected on a frit and washed with cold (0° C.) toluene (250 mL). The filter cake was dried under nitrogen to provide 446.5 g (1.52 mol, 67.5%) of a 20:1 mixture of 3 and its regioisomer as a white solid.

$^1$H NMR (CDCl$_3$; 250 MHz): δ7.28–7.18 (m, 2H), 7.18–7.00 (m, 7H), 6.19 (dt, J=18.2 and 1.9 Hz, 1H), 4.88 (dd, J=3.5 and 1.9 Hz, 2 H).

$^{13}$C NMR (CDCl$_3$; 62.9 MHz): δ150.6, 148.2, 148.1, 147.8, 122.7, 122.6, 122.4, 112.4, 112.3, 112.1, 66.9.

EXAMPLE 3

Preparation of 2-allyl alcohol (4)

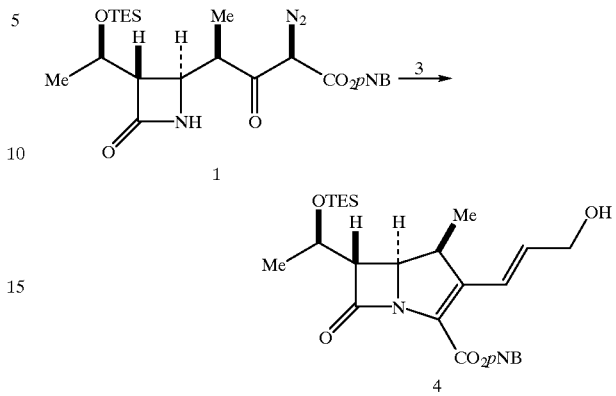

A solution of diazo compound 1 (100 g), zinc chloride (200 mg) and rhodium octanoate (0.9 g) in dry methylene chloride (450 mL) was refluxed for 4 hr. Diisopropylamine (30.8 mL) and triethylamine (10 mL) were added to the reaction mixture at −75° C. After 10 min., trifluoromethanesulfonic anhydride (38.9 mL) were added to the mixture keeping the internal temperature below −65° C. The resulting triflate solution was aged at −75° C. for 2 hr.

'In a separate flask, diborate 3 from Example 2 (76 g) was stirred in a mixture of THF (120 mL), 3 M aqueous potassium carbonate (43 mL) and phosphate buffer (1.3 M, pH=7.6, 360 mL) under argon atmosphere for 2 h at 22° C.

The catalyst for this reaction was prepared as follows: To a solution of triphenylphosphine (12.5 g) in dry THF (1.2 L) was added palladium acetate (3.56 g) under argon atmosphere. The mixture was stirred at 22° C. until it became homogeneous solution (20 min). The solution was heated to 68° C. for 30 min. Prior to the coupling reaction, the solution was cooled to 22° C.

The triflate and catalyst solutions were added to the above diborate mixture under an argon atmosphere. The resulting mixture was stirred at 35° C. The reaction was complete in 1 h with an assay yield of 93%.

The reaction mixture was diluted with a mixture of ethyl acetate (1.2 L) and hexanes (300 mL) and stirred for 10 min at room temperature. The mixture was filtered through Solka-Flock. The organic layer was separated and washed water (3×500 mL). The organic layer was concentrated to about 250 mL and hexanes was added to the solution until the product crystallized. Allyl alcohol 4 (82.5 g) was isolated in 81% isolated yield as crystals. The mother liquor contained 10.2 g (10%) of 4.

$^1$H NMR (250 MHz, CDCl$_3$): δ8.22 (m, 2H), 7.68 (d, J=8.7 Hz, 2H), 7.31 (d, J=16.2 Hz, 1H), 6.19 (dt, J=16.2 and 5.5 Hz, 1H), 5.46 (d, J=13.9 Hz, 1H), 5.27 (d, J=13.9 Hz, 1H), 4.35–4.16 (m, 4H), 3.37 (m, 1H), 3.23 (dd, J=6.2 and 2.7 Hz, 1H), 1.49 (t, J=5.9 Hz, 1H), 1.29 (d, J=6.2 Hz, 3H), 1.22 (d, J=7.9 Hz, 3H), 0.94 (t, J=7.8 Hz, 9H), 0.60 (m, 6H).

$^{13}$C NMR (62.9 MHz, CDCl$_3$): δ172.9, 160.9, 148.7, 147.5, 143.0, 137.4, 128.1, 125.2, 123.7, 122.4, 66.0, 65.2, 63.3, 59.1, 56.4, 39.5, 22.6, 16.8, 6.8, 4.9.

EXAMPLE 4

Preparation of 2-formyl carbapenem from 2-allyl alcohol (4)

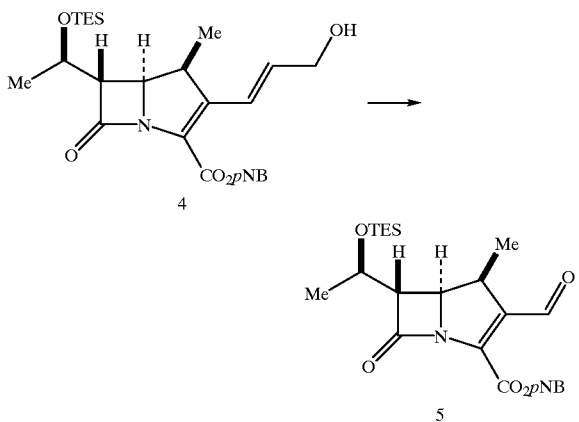

Into a 3-L three-necked flask equipped with a mechanical stirrer and a thermal couple was charged potassium osmate dihydrate (2.61 g), 4-methylmorpholine N-oxide (34.4 g), 4-morpholineethanesulfonic acid monohydrate (84.2 g), and water (250 mL). This mixture was stirred at 30° C. until potassium osmate dihydrate dissolved. A solution of 2-allylic alcohol 4 from Example 3 (53.6 g, 93.2 wt %) in THF (500 mL) was added in the rate in keeping the temperature lower than 30° C. This solution was stirred at 30° C. for 1.5 h. The organic layer was separated and washed with brine-water (3:7, 250 ml). A mixture of THF (200 mL) and water (250 mL) was added to the organic layer and sodium periodate (36.0 g) was added to the resulted mixture. After stirring 10 min at 30° C., ethyl acetate (1 L) and water (1 L) was added. The organic layer was washed with 1 M sodium thiosulfate (2×250 mL) and brine (250 mL). To the solution was added silica gel (100 g). Evaporation of the solvent gave a dark brown residue which was filtered through a silica gel pad (50 g) using a mixture of ethyl acetate and heptane (1:6, 2 L). Evaporation of the filtrate gave 2-formyl carbapenem 5 as yellowish crystals (24.5 g, 90 wt %, 46.7% yield).

$^1$H-NMR (250 MHz, CDCl$_3$): δ10.4 (s, 1H), 8.24 (m, 2H), 7.67 (d, J=8.6 Hz, 2H), 5.51 (ABq, J=13.6 Hz, 1H), 5.36 (ABq, J=13.6 Hz, 1H), 4.36 (dd, J=10.5 and 3.5 Hz, 1H), 4.30 (qd, J=6.2 and 5.0 Hz, 1H), 3.51 (dq, J=10.2 and 7.3 Hz, 1H), 3.41 (dd, J=4.5 and 3.7 Hz, 1H), 1.24 (d, J=6.6 Hz, 6H), 0.94 (t, J=7.8 Hz, 9H), 0.63 (m, 6H).

$^{13}$C-NMR (62.9 MHz, CDCl$_3$): δ188.9, 172.8, 159.2, 147.8, 143.0, 141.8, 140.0, 128.4, 123.7, 66.4, 65.0, 60.9, 56.2, 38.0, 22.2, 16.2, 6.70, 4.82.

EXAMPLE 5

Preparation of 2-hyroxymethyl carbapenem (6) from 2-formyl carbapenem (5)

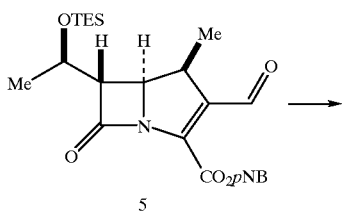

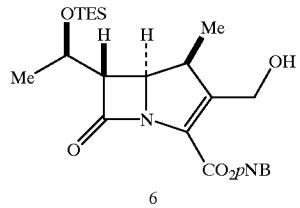

To a 500 mL round-bottom flask was added the aldehyde 5 from Example 4 (13.5 g) with 250 ml of dry THF. Borane THF complex (1.0 M in THF; 26.1 ml) was added via syringe at −15° C. and the resulting solution was stirred for 10 minutes. The reaction solution was quenched into a cold mixture of ethyl acetate and water (800 ml). The organic layer contained 2-hydroxymethyl carbapenem (6) in 94% yield by HPLC analysis. The organic layer was dried over magnseium sulfate and solvent switched to heptane. The solution was concentrated to ~50 ml and the resulting crystals were collected by filtration. The cake was washed with 25 ml of heptane. The crystalline product (12 g) (89%) was isolated.

EXAMPLE 6

Preparation of 2-hyroxymethyl carbapenem (6) from 2-vinyl carbapenem (2)

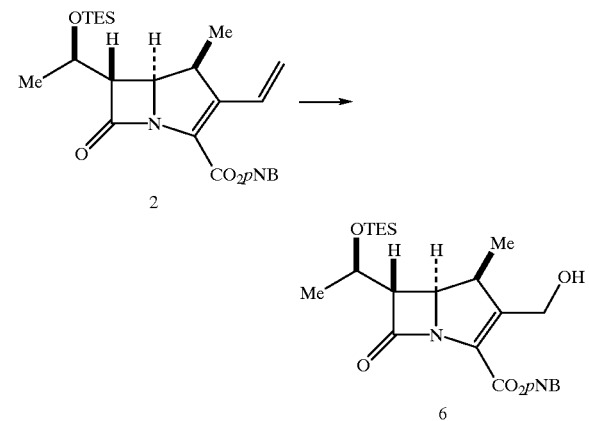

Into a 500 mL three-necked flask equipped with a mechanical stirrer and a thermal couple was charged potassium osmate dihydrate (75.5 mg), 2-vinyl carbapenem 2 from Example 1 (4.0 g), and phosphate buffer (pH=6.0, 2 M, 130 mL). Sodium periodate (5.3 g) was added over 5 h. Brine (100 mL) was added and then layers was separated. The aqueous layer was extracted with ethyl acetate (100 mL). The combined organic layers were concentrated to 50 mL and added slowly into a suspension of sodium borohydride (3.1 g) and zinc chloride (5.6 g) in ethyl acetate (200 mL) under 0° C. After stirred 1 h at room temperature, the suspension was filtered. Evaporation of the filtrate gave a brown oil, which was passed though a silica gel column (8 g of silica gel, hexanes and ethyl acetate=10:1). Recrystallization from a mixture of ethyl acetate and hexanes gave 6 (1.79 g, 44%).

What is claimed is:

1. A process of synthesizing a compound of formula 3:

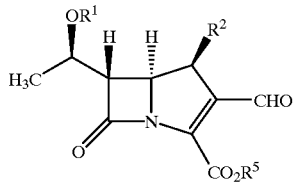

wherein $R^1$ represents H or a suitable protecting group for an alcohol; $R^2$ represents H or methyl; and $R^5$ represents a carboxy protecting group comprising adding a compound of formula 2:

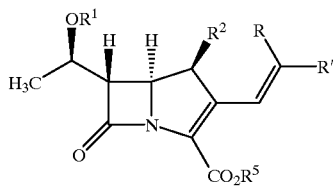

wherein $R^1$, $R^2$ and $R^5$ are described above and R and R' independently represent H, alkyl, O-alkyl, S-alkyl, O-aryl, S-aryl, or aryl or R is H and R' is $CH_2OH$; said alkyl optionally substituted with 1–3 groups of N, S, O, and halo; to a solvent in the presence of a catalyst and oxidizing agent to produce a compound 3.

2. A process according to claim 1 wherein the catalyst comprises $RuCl_3$, $RuO_2$, $K_2OsO_4.2H_2O$, $KMnO_4$, and $OsO_4$ or a combination thereof.

3. A process according to claim 1 wherein the solvent comprises tetrahydrofuran (THF), ethylacetate (EtOAc), $H_2O$, $C_{1-6}$ alcohol, dichloromethane, acetonitrile and acetone or a combination thereof.

4. A process according to claim 1 in which an oxidizing agent selected from the group consisting of $NaIO_4$, $HIO_4$, N-methylmorpholine (NMM), N-methylmorpholine N-oxide (NMO)-$NaIO_4$, $NaIO_4$-$HIO_4$, or a combination thereof is added.

5. A process according to claim 1 which is conducted at a temperature of about 0° C. to about 80° C.

6. A process according to claim 5 which is conducted at a temperature of 20° C. to about 35° C.

7. A process according to claim 1 wherein R and R' are hydrogen or R is H and R' is $CH_2OH$.

8. A process according to claim 1 wherein $R^1$ is selected from the group consisting of hydrogen, trialkylsilyl, diarylalkylsilyl, aryldialkylsilyl or trityl TMS (trimethylsilyl), TES (triethylsilyl), TBDMS (t-butyldimethylsilyl), diarylalkylsilyl and aryldialkylsilyl.

9. A process according to claim 8 wherein $R^1$ is TMS, TES or TBDMS.

10. A process according to claim 1 wherein $R^5$ is selected from the group consisting of allyl, benzhydryl, 2-naphthylmethyl, benzyl, silyl groups t-butyldimethylsilyl (TBDMS), trimethylsilyl, (TMS), triethylsilyl (TES), phenacyl, p-methoxybenzyl, o-nitrobenzyl, p-methoxyphenyl, p-nitrobenzyl (pNB), 4-pyridylmethyl and t-butyl.

11. A process according to claim 8 wherein $R^1$ is TBS (t-butyldimethylsilyl) and the catalyst is $OsO_4$, $RuCl_3$ or a combination thereof.

12. A process according to claim 11 in which an oxidant comprising $NaIO_4$, $HIO_4$ or $NaIO_4$-$HIO_4$ is added.

13. A process according to claim 11 which is conducted at a temperature of about 20° C. to about 30° C.

14. A process according to claim 8 wherein $R^1$ is TES and the catalyst is $OsO_4$, or $K_2OsO_4.2H_2O$.

15. A process according to claim 14 in which an oxidant comprising $NaIO_4$, $HIO_4$, or NMO(N-methylmorpholine N-oxide)-$NaIO_4$ is added.

16. A process according to claim 14 which is conducted at a temperature of about 20° C. to about 30° C.

17. A process according to claim 14 in which the pH is maintained at about 4 to about 8.

18. A process according to claim 14 in which a base selected from the group consisting of pyridine, triethylamine, triethylamine, trimethylamine, ethyldimethylamine, tri-n-propylamine, 1,8-diazabicyclo[5.4.0]undec-7-ene (DBU), imidazole, lutidine, collidine, 4-dimethylaminomethylpyridine, N,N,N',N'-tetramethylethylenediamine (TMEDA), N-methylmorpholine (NMM) is added.

19. A process for the synthesis of a compound of formula 4:

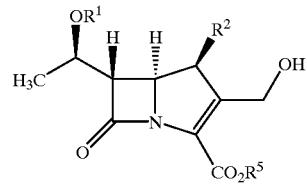

is disclosed wherein $R^1$ represents H or a suitable protecting group for an alcohol; $R^2$ represents H or methyl; and $R^5$ represents a carboxy protecting group comprising adding a compound of formula 2:

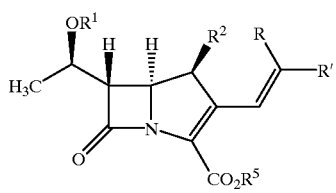

wherein $R^1$, $R^2$ and $R^5$ are described above and R and R' independently represent H, alkyl, O-alkyl, S-alkyl, O-aryl, S-aryl, or aryl; or R is H and R' is $CH_2OH$, said alkyl optionally substituted with 1–3 groups of N, S, O, and halo; to a solvent in the presence of a catalyst and oxidizing agent to produce a compound 3:

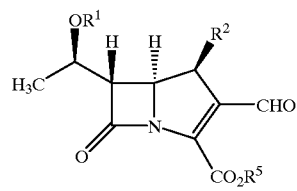

wherein $R^1$, $R^2$ and $R^5$ are described above; reducing a compound of formula 3 with a reducing agent to produce a compound of formula 4.

20. A process according to claim 19 wherein the reducing agent selected from the group consisting of $Cp_2TiCl_2$/$NaBH_4$, $ZnCl_2$/$NaBH_4$, $BH_3 \cdot SMe_2$, and $BH_3 \cdot THF$.

21. A process according to claim 19 wherein the catalyst comprises $RuCl_3$, $RuO_2$, $K_2OsO_4 \cdot 2H_2O$, and $KMnO_4$, $OsO_4$ or a combination thereof, the solvent comprises tetrahydrofuran (THF), ethylacetate (EtOAc), $H_2O$, $C_{1-6}$ alcohol, dichloromethane, acetonitrile and acetone or a combination thereof and the temperature is at about about 0° C. to about 80° C.

22. A process according to claim 19 in which an oxidizing agent comprising $NaIO_4$, $HIO_4$, N-methylmorpholine (NMM), N-methylmorpholine N-oxide (NMO)-$NaIO_4$, $NaIO_4$-$HIO_4$, or a combination thereof is added.

23. A process according to claim 1 wherein R and R' are hydrogen or R is H and R' is $CH_2OH$, $R^1$ is TMS, TES or TBDMS and $R^5$ is selected from the group consisting of allyl, benzhydryl, 2-naphthylmethyl, benzyl, silyl groups such as t-butyldimethylsilyl (TBDMS), trimethylsilyl, (TMS), triethylsilyl (TES), phenacyl, p-methoxybenzyl, o-nitrobenzyl, p-methoxyphenyl, p-nitrobenzyl (pNB), 4-pyridylmethyl and t-butyl.

24. A process according to claim 23 wherein $R^1$ is TBS and the catalyst is $OsO_4$, $RuCl_3$ or a combination thereof.

25. A process according to claim 24 in which an oxidant selected from the group consisting of $NaIO_4$, $HIO_4$ and $NaIO_4$-$HIO_4$ is added.

26. A process according to claim 23 which is conducted at a temperature of about 20° C. to about 30° C.

27. A process according to claim 23 wherein $R^1$ is TES and the catalyst is $OsO_4$, or $K_2OsO_4 \cdot 2H_2O$.

28. A process according to claim 27 in which an oxidant selected from the group consisting of $NaIO_4$, $HIO_4$ or NMO(N-methylmorpholine N-oxide)-$NaIO_4$ is added.

29. A process according to claim 28 which is conducted at a temperature of about 20° C. to about 30° C.

30. A process according to claim 27 in which the pH is maintained at about 4 to about 8.

31. A process according to claim 27 in which a base selected from the group consisting of pyridine, triethylamine, triethylamine, trimethylamine, ethyldimethylamine, tri-n-propylamine, 1,8-diazabicyclo[5.4.0]undec-7-ene (DBU), imidazole, lutidine, collidine, 4-dimethylaminomethylpyridine, N,N,N',N'-tetramethylethylene-diamine (TMEDA), N-methylmorpholine (NMM) is added.

32. A compound of formula 3:

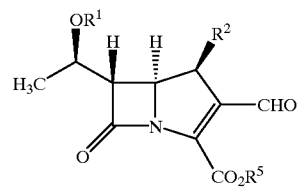

wherein $R^1$ represents t-butyldimethylsilyl (TBS), trimethylsilyl, (TMS), or triethylsilyl (TES), $R^2$ represents $C_{1-3}$ alkyl and $R^5$ represents para-nitrobenzyl (pNB).

* * * * *